(12) United States Patent
Hu et al.

(10) Patent No.: US 8,992,815 B2
(45) Date of Patent: Mar. 31, 2015

(54) PRODUCTION OF ORGANIC COMPOUND NANOPARTICLES WITH HIGH REPETITION RATE ULTRAFAST PULSED LASER ABLATION IN LIQUIDS

(75) Inventors: Zhendong Hu, Ann Arbor, MI (US); Yong Che, Ann Arbor, MI (US)

(73) Assignee: IMRA America, Inc., Ann Arbor, MI (US)

(*) Notice: Subject to any disclaimer, the term of this patent is extended or adjusted under 35 U.S.C. 154(b) by 794 days.

(21) Appl. No.: 12/951,496

(22) Filed: Nov. 22, 2010

(65) Prior Publication Data
US 2011/0196044 A1    Aug. 11, 2011

Related U.S. Application Data

(60) Provisional application No. 61/302,984, filed on Feb. 10, 2010.

(51) Int. Cl.
*B01J 13/00* (2006.01)
*B82Y 40/00* (2011.01)
*A61K 9/14* (2006.01)
*B23K 26/06* (2014.01)

(52) U.S. Cl.
CPC . *B82Y 40/00* (2013.01); *A61K 9/14* (2013.01); *B23K 26/0635* (2013.01); *Y10S 977/889* (2013.01); *B01J 13/0086* (2013.01); *Y10S 977/901* (2013.01)
USPC ............... 264/400; 241/1; 241/21; 241/23; 977/901; 977/889

(58) Field of Classification Search
USPC ............... 264/400; 977/901; 241/1, 21, 23; 424/489
See application file for complete search history.

(56) References Cited

U.S. PATENT DOCUMENTS 5,390,864 A * 2/1995 Alexander ............ 241/39
5,585,020 A * 12/1996 Becker et al. ........ 219/121.85
(Continued)

FOREIGN PATENT DOCUMENTS

JP    2004167316 A    6/2004
JP    2004267918 A    9/2004
(Continued)

OTHER PUBLICATIONS

Nichols et al. (Laser ablation of a platinum target in water. I. Ablation mechanisms. J. App. Phy. 100 11491 (2006)).*
(Continued)

*Primary Examiner* — Atul P. Khare
(74) *Attorney, Agent, or Firm* — Dickinson Wright PLLC (57) ABSTRACT

Disclosed is a method of producing a chemically pure and stably dispersed organic nanoparticle colloidal suspension using an ultrafast pulsed laser ablation process. The method comprises irradiating a target of an organic compound material in contact with a poor solvent with ultrashort laser pulses at a high repetition rate and collecting the nanoparticles of the organic compound produced. The method may be implemented with a high repetition rate ultrafast pulsed laser source, an optical system for focusing and moving the pulsed laser beam, an organic compound target in contact with a poor solvent, and a solvent circulating system to cool the laser focal volume and collect the produced nanoparticle products. By controlling various laser parameters, and with optional poor solvent flow movement, the method provides stable colloids of dispersed organic nanoparticles in the poor solvent in the absence of any stabilizing agents.

26 Claims, 8 Drawing Sheets

(56) References Cited

U.S. PATENT DOCUMENTS

| | | | |
|---|---|---|---|
| 6,467,922 | B1 | 10/2002 | Blanc et al. |
| 6,653,226 | B1 | 11/2003 | Reid |
| 6,700,660 | B2 | 3/2004 | Sabsabi et al. |
| 7,133,187 | B2 | 11/2006 | Johnson |
| 7,527,824 | B2 * | 5/2009 | Becker et al. .................. 427/212 |
| 7,597,278 | B2 | 10/2009 | Asahi et al. |
| 8,512,436 | B2 * | 8/2013 | Kawasaki et al. ............... 75/345 |
| 2002/0003179 | A1 * | 1/2002 | Verhoff et al. .................. 241/21 |
| 2005/0243396 | A1 * | 11/2005 | Fujii et al. ..................... 359/224 |
| 2005/0287308 | A1 * | 12/2005 | Becker et al. .................. 427/561 |
| 2007/0029185 | A1 * | 2/2007 | Tung ........................ 204/157.41 |
| 2008/0006524 | A1 | 1/2008 | Liu et al. |
| 2008/0062491 | A1 | 3/2008 | Nakamura et al. |
| 2008/0237376 | A1 | 10/2008 | Asahi et al. |
| 2009/0053523 | A1 | 2/2009 | Kawasaki et al. |
| 2009/0246530 | A1 | 10/2009 | Murakami et al. |
| 2012/0282134 | A1 * | 11/2012 | Liu et al. ....................... 420/591 |

FOREIGN PATENT DOCUMENTS

| | | |
|---|---|---|
| JP | 2005008524 A | 1/2005 |
| JP | 2005238342 A | 9/2005 |
| JP | 2007306950 A | 11/2007 |
| WO | 2006030605 A1 | 6/2006 |
| WO | 2007132853 A1 | 11/2007 |
| WO | WO 2009117451 A1 * | 9/2009 |

OTHER PUBLICATIONS

Chen et al. Laser ablation method: use of surfactants to form the dispersed Ag nanoparticles. Colloids and Surfaces A: Physiochemical and Engineering Aspects 197 (2002) 133-139.*

T. Asahi et al., "Laser Fabrication and Spectroscopy of Organic Nanoparticies", Accounts of Chemical Research, vol. 41, No. 12, 2008.

S. Bisht et al., "Polymeric Nanoparticle-Encapsulated Curcumin ("nanocurcumin"): a novel strategy for human cancer therapy", Journal of Nanobiotechnology, vol. 5:3, 2007.

Jing Cui et at., "Enhancement of oral absorption of curcumin by self-microemulsifying drug delivery systems", International Journal of Pharmaceutics vol. 371, 148-155, 2009.

Elaboudi et al., "From polymer films to organic nanoparticles suspensions by means of excimer laser ablation in water", Appl. Phys. A, vol. 93, 827-831, 2008.

B. Liu et al., "Ultrafast lasers produce nanoparticles", Laser Focus World, vol. 43, 74 (2007).

B. Liu et al., "Nanoparticle generation in ultrafast pulsed laser ablation of nickel", Applied Physics Letters, vol. 90, 044103 (2007).

T.H. Marczylo et al., "Comparison of systemic availability of curcumin with that of curcumin formulated with phosphatidylcholine", Cancer Chemother Pharmacol, vol. 60, 171-177 (2007).

T. Sugiyama et al "Formation of 10 nm-sized Oxo(phtalocyaninato)vanadium(IV) Particles by Femtosecond Laser Ablation in Water", Chemistry Letters vol. 33, No. 6, 724 2004.

Y, Tamaki et al., "Tailoring nanoparticles of aromatic and die molecules by excimer laser irradiation", Applied Surface Science, vol. 168, 85-88 2000.

R. Yasukuni et al., "Size-Dependent Optical Properties of Dendronized Perylenediimide Nanoparticle Prepared by Laser Ablation in Water", Japanese Journal of Applied Physics, vol. 48, 065002, 2009.

International Search Report; Dated Apr. 4, 2011 (2 pages).

* cited by examiner

PRODUCTION OF ORGANIC COMPOUND NANOPARTICLES WITH HIGH REPETITION RATE ULTRAFAST PULSED LASER ABLATION IN LIQUIDS

RELATED APPLICATIONS

This application claims the benefit of U.S. provisional application Ser. No. 61/302,984 filed Feb. 10, 2010.

STATEMENT REGARDING FEDERALLY SPONSORED RESEARCH

NONE

TECHNICAL FIELD

This invention relates generally to use of ultrafast pulsed laser ablation to generate stable hydrocolloids of nanoparticles having an average diameter of 100 nanometers or less from organic compounds.

BACKGROUND

Most sugars are highly soluble in water, but not all solid organic compounds can be dissolved in water with reasonable solubility. It is highly desirable to dissolve many solid organic compounds in water, or to disperse solid organic compounds into water to form a stable hydrocolloid. It would be most beneficial to create a method that was applicable to the widest variety of organic solids. Curcumin, 1,7-bis(4-hydroxy-3-methoxyphenyl)-1,6-heptadiene-3,5-dione, is a natural yellow-orange dye extracted from the rhizomes of *Curcuma longa* L. and it has a variety of biological activities and pharmacological actions. Unfortunately, curcumin is not water soluble and that limits its' effective bioavailability in many systems. Many attempts have been made to disperse curcumin into water to improve its bioavailability. A self-microemulsifying drug delivery system comprising a microemulsion of curcumin with oils and surfactants was reported to improve the solubility of curcumin in water. Jing Cui, Bo Yu, Yu Zhao, Weiwei Zhu, Houli Li, Hongxiang Lou, Guangxi Zhai, "Enhancement of oral absorption of curcumin by self-microemulsifying drug delivery systems", International Journal of Pharmaceutics Vol. 371, 148-155, 2009. A curcumin-phospholipid complex was reported to greatly increase both the bioavailability and the formation of metabolites as compared to unformulated curcumin. T. H. Marczylo, R. D. Verschoyle, D. N. Cooke, P. Morazzoni, W. P. Steward, A. J. Gescher, "Comparison of systemic availability of curcumin with that of curcumin formulated with phosphatidylcholine", Cancer Chemother. Pharmacol., Vol. 60, 171-177, 2007. A polymeric nanoparticle-encapsulated curcumin, nicknamed "nanocurcumin", was also reported as a novel strategy to improve the bioavailability of curcumin. S. Bisht, G. Feldmann, S. Soni, R. Ravi, C. Karikar, A. Maitra and A. Maitra, "Polymeric nanoparticle-encapsulated curcumin ("nanocurcumin"): a novel strategy for human cancer therapy", Journal of Nanobiotechnology, Vol. 5:3, 2007. All of these methods involve using other chemical compounds in addition to the desired organic compound, in these references curcumin, to form a complex having improved bioavailability and solubility in water.

Pulsed laser ablation of metal or metal-alloy targets in liquids is one of the physical methods used to produce metal and metal-alloy nanoparticles. In this process, a pulsed laser beam is focused on the surface of a target that is submerged in a liquid. The ablated material re-nucleates in the liquid and forms nanoparticles. In recent years, there have been reports of applying pulsed laser ablation techniques to very small volumes of organic nanoparticle preparations in which organic microcrystalline powders suspended in a poor solvent are irradiated with intense laser pulses, which induce fragmentation of the initial crystals. See for example, Yoshiaki Tamaki, Tsuyoshi Asahi, and Hiroshi Masuhara, "Tailoring nanoparticles of aromatic and dye molecules by excimer laser irradiation", Applied Surface Science, Vol. 168, 85-88, 2000; Teruki Sugiyama, Tsuyoshi Asahi, and Hiroshi Masuhar, "Formation of 10 nm-sized Oxo(phtalocyaninato)vanadium (IV) Particles by Femtosecond Laser Ablation in Water", Chemistry Letters Vol. 33, No. 6, 724, 2004; and T. Asahi, T. Sugiyama, and H. Masuhara, "Laser Fabrication and Spectroscopy of Organic Nanoparticles", Accounts of Chemical Research, Vol. 41, No. 12, 2008. A poor solvent is a liquid that the target organic material has low to no solubility in. After a sufficient amount of exposure to the laser beam, the opaque suspension of organic microcrystalline powders is converted into a transparent colloidal suspension. This laser ablation approach appears to convert organic microcrystalline powders directly into stable nanocolloidal suspensions without additives and chemicals. All of the results reported to date have been conducted in a cuvette with a total volume of 3 milliliters, and it is difficult to scale up from this small volume to mass production of organic nanoparticles with this laser ablation approach. Obviously, the pulsed laser ablation of an organic microcrystalline powder suspension in a fixed volume small cuvette cannot maintain a constant efficiency of generation of organic nanoparticles because of the decreasing amount of microcrystalline powder available during the ablation process. Similar results were also reported by several other groups, see for example I. Elaboudi, S. Lazare, C. Belin, D. Talaga. And C. Labrugère, "From polymer films to organic nanoparticles suspensions by means of excimer laser ablation in water", Appl. Phys. A, Vol 93, 827-831, 2008 and R. Yasukuni, M. Sliwa, J. Hofkens, F. C. De Schryver, A. Herrmann, K. Mullen, and T. Asahi, "Size-Dependent Optical Properties of Dendronized Perylenediimide Nanoparticle Prepared by Laser Ablation in Water", Japanese Journal of Applied Physics, Vol. 48, 065002, 2009.

It is desirable to develop a method for formation of nanoparticles from organic compounds that are poorly soluble in water and other liquids to increase their bioavailability and usefulness in biological systems. In addition, it would be useful to develop a production method for organic nanoparticles that avoids coagulation, eliminates any requirement for a stabilizing agent, and that provides for rapid throughput and scale up to mass production levels.

SUMMARY OF THE INVENTION

In general terms, this invention provides a method and system for producing chemically pure and stable colloidal suspensions of nanoparticles from organic compounds using laser ablation. The method comprises the steps of generating a high repetition rate ultrafast pulsed laser beam; providing an organic compound target and irradiating the organic compound target with the pulsed laser beam, the target positioned in a liquid that is substantially transparent at a wavelength of the pulsed laser beam, the irradiation generating a nanoparticle suspension of the target in the liquid by ablation; and producing one or both of a flow of the liquid relative to a surface of the target and relative motion between the pulsed laser beam and the target. The method and system are highly efficient and are capable of high production rates for organic nanoparticle colloidal suspensions. The colloidal suspensions are stable at 25° C. for at least one week in the absence of any stabilizing agents. In the present specification and claims the terms "nanoparticle" or "nanoparticles" with respect to particles produced according to the present invention means particles with an average diameter of 100 nanometers or less. A poor solvent is defined as a liquid wherein the target organic material has a very low solubility if any solubility at all.

These and other features and advantages of this invention will become more apparent to those skilled in the art from the detailed description of a preferred embodiment. The drawings that accompany the detailed description are described below.

DETAILED DESCRIPTION OF THE INVENTION

The present invention is directed toward a laser system for producing stable nanoparticle colloidal suspensions from organic materials using an ultrafast pulsed laser ablation process.

Figure 1:
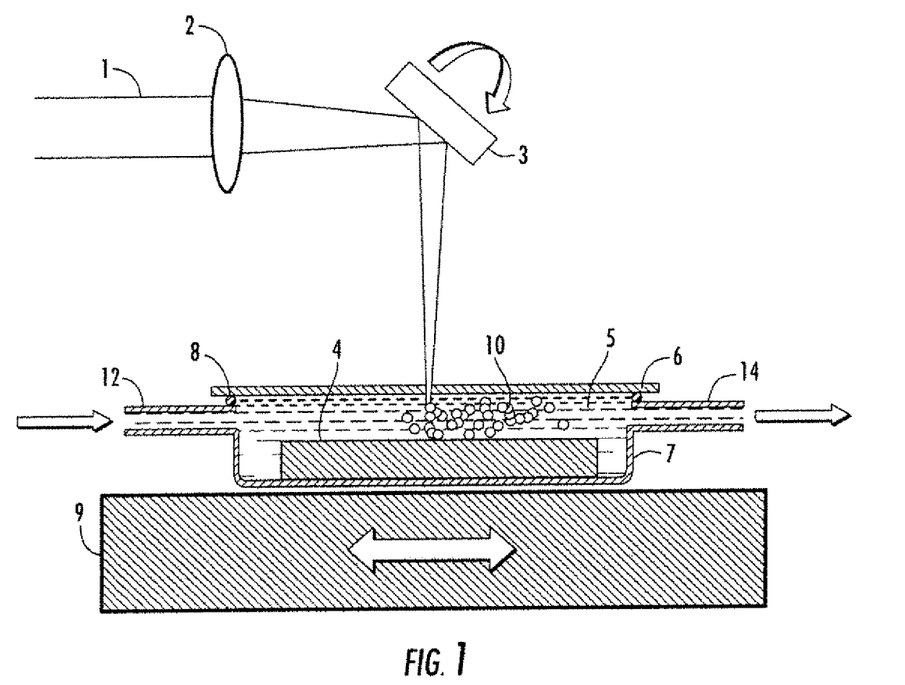
FIG. 1 schematically illustrates a laser-based system for producing organic nanoparticles in a liquid according to the present invention.

FIG. 1 schematically illustrates a laser-based system for producing organic nanoparticles in a liquid in accordance with the present invention. In one embodiment a laser beam 1 is received from a ultrafast pulse source, not shown, and focused by a lens 2. The source of the laser beam 1 can be any suitable ultrafast pulsed laser source capable of providing a pulse duration, repetition rate and/or power level as discussed below. The focused laser beam 1 then passes from the lens 2 to a guide mechanism 3 for controlling movement of the laser beam 1. The guide mechanism 3 can be any of those known in the art including, by way of example only, piezo-mirrors, acousto-optic deflectors, rotating polygons, vibrating mirror, and prisms. Preferably the guide mechanism 3 is a vibrating mirror 3 to enable controlled and rapid movement of the focused laser beam 1. The guide mechanism 3 directs the focused laser beam 1 at a target 4. In one embodiment, the target 4 is a compressed pellet of an organic compound that is being converted into nanoparticles. The compressed pellet can be formed from a variety of powder sources of the organic material. It is preferred to begin with a powdered source of the organic compound that has an average particle size of from submicron to millimeter (mm) size depending on the softness of the starting powder, preferably from submicron to submillimeter size. The powdered source material can then be compressed into a pellet using a mold and pressure. The pressures used depend on the starting material, but the target 4 pellet must be self sustaining and able to maintain integrity in a container 7 with a flow of a liquid 5 as described below. The size of the compressed target 4 is larger than 1 mm in at least one dimension. Alternatively, the target 4 can be another source of the organic compound material such as: a film of the organic compound that has been deposited onto a substrate; a bulk material of an organic compound with at least one dimension that is larger than 5 mm; a stream of the bulk organic compound which has been ejected from a nozzle into the liquid 5; or a paste of the bulk organic compound that has been introduced into the liquid 5. Any of these can serve as the target 4 material in the present invention. At least a portion of the target 4 is in contact with the liquid 5, preferably the target 4 is submerged a distance of from several millimeters to preferably less than 1 centimeter below the surface of a liquid 5. Preferably, the target 4 is positioned in a container 7 having a removable glass window 6 on top of the container 7. An O-ring type of seal 8 is placed between the glass window 6 and the top of the container 7 to prevent the liquid 5 from leaking out of the container 7. The container 7 includes an inlet 12 and an outlet 14 so the liquid 5 can be passed over the target 4 and so that it can be re-circulated. The container 7 is optionally placed on a motion stage 9 that can produce translational motion of the container 7 and movement of the liquid 5. Flow of the liquid 5 is used to carry generated nanoparticles 10 out of the container 7 to be collected elsewhere. The flow of liquid S over the target 4 also cools the laser focal volume. The flow rate and volume of liquid S should be sufficient to fill the gap between the target 4 and the glass window 6 as shown. In addition, it must be sufficient to prevent any gas bubbles generated during the laser ablation from staying on the glass window 6. The liquid 5 can be any liquid that is largely transparent to the wavelength of the laser beam 1 and that preferably is a poor solvent for the target material 4. In one embodiment, the liquid 5 is deionized water, preferably having a resistivity of greater than 0.05 MOhm·cm, and more preferably greater than 1 MOhm·cm.

The ultrafast pulsed laser beam 1 preferably has a pulse duration of 500 picoseconds or less, preferably from about 10 femtoseconds to 500 picoseconds, more preferably from 10 femtoseconds to 200 picoseconds, and most preferably from 100 femtoseconds to 10 picoseconds. The pulse repetition rate is preferably from 1 Hz to 100 MHz, more preferably from 10 kHz to 10 MHz, and most preferably from 100 kHz to 5 MHz. A preferred wavelength is about 1045 nanometers, however any suitable wavelength of from about 400 nanometers to 4000 nanometers may be used. At a wavelength of 1045 nanometers a layer of water of a few millimeters in thickness over the target 4 has a negligible absorption at this wavelength. Preferably the laser beam 1 has a pulse energy in the range of about 1 nano-Joules to 10 mili-Joules, more preferably in the range from 100 nano-Joules to 10 micro-Joules for generation of nanoparticles 10. Preferably the laser beam 1 has a laser fluence at the focus spot on the surface of target 4 in the range of from about 100 micro-Joules/cm$^2$ to 100 Joules/cm$^2$, more preferably from 10 milli-Joules/cm$^2$ to 5 Joules/cm$^2$.

In one embodiment the guide mechanism 3 is a vibrating mirror 3 that is configured for fast rastering or other movement of the laser beam 1 on the surface of the target 4. The vibration frequency of mirror 3 is preferably 10 Hz or greater and preferably it has an angular amplitude of 0.1 mrad or greater and more preferably of 1.0 mrad or greater, such that a rastering speed on the surface of the target 4 is 0.01 meters per second or greater and most preferably 0.1 meters per second or greater. Such a mirror 3 can be a piezo-driven mirror, a galvanometer mirror, or other suitable apparatus for movement of the laser beam 1.

In one embodiment, flow of the liquid 5 through the container 7 is carried out by a circulation system, with a flow speed preferably of 1.0 milliliter per second or greater and more preferably of 10.0 milliliter per second or greater. Flow of liquid 5 is necessary to uniformly distribute the generated nanoparticles 10 in the liquid 5 and to remove them from the container 7. It is preferred to maintain a sufficient volume of the liquid 5 to avoid any fluctuations in the thickness of liquid 5 above the target 4. If the liquid 5 thickness varies it can change the optical path properties of the laser beam 1 and cause a broader distribution of sizes of the generated nanoparticles 10. The optical window 6 above the flowing liquid 5 helps to keep a constant thickness of liquid 5 above the target 4. When a circulation system is not available, introducing lateral vibration movement, for example perpendicular to the laser beam 1, as indicated in FIG. 1, to the motion stage 9 can also cause liquid 5 flow locally across the ablation spot. The motion stage 9 preferably has a vibration frequency of several Hz and an amplitude of several millimeters. A shaker can also be used to circulate the liquid 5, wherein the circular movement of the shaker causes the liquid 5 in the container 7 to have a circular movement too, therefore the organic nanoparticles 10 can distribute evenly in the liquid 5. With either of these two methods of circulating the liquid 5, the glass window 6 is not necessary; however, the use of either will introduce non-uniformity into the thickness of the liquid 5 above the target 4 and will cause a broader size distribution of the nanoparticles 10.

The present invention provides a system and method for formation of stable and chemically pure nanoparticle colloidal suspensions from organic compounds. By stable it is meant that the hydro colloidal, if produced in water, or colloidal suspension if produced in another liquid is stable with no aggregation of the particles after storage at 25° C. for at least 7 days and more preferably stable for at least 2 months under these conditions. By chemically pure it is meant that the colloidal suspension is composed only of the organic materials found in the target 4 and the liquid 5 from which the colloidal suspension is derived. There is no need for added stabilizing agents or surface active agents to maintain the colloid in a stable state. The present inventors have discovered that through proper control of laser parameters including pulse duration, pulse energy, pulse repetition rate, and movement of the laser beam 1 over the target 4 such stable nanoparticle colloidal suspensions can be produced. Both the laser beam 1 movement rate and the liquid 5 flow rate can be used to aid the process by controlling heat accumulation derived from the preferred high pulse repetition rates used in the present invention.

In the present invention ultrashort pulse widths are preferred. It is preferred that the pulse width or pulse duration range from 10 femtoseconds to 200 picoseconds and more preferably from 100 femtoseconds to 10 picoseconds. These short duration pulses are believed to enhance ablation efficiency because of a very high peak power and a small heat-affected zone at the ablation site.

Previous studies of laser ablation to produce nanoparticles from metal and metal oxides have found that low pulse energy, more precisely a low laser fluence at or near the ablation threshold is preferred for nanoparticle generation from these inorganic target materials. See for example, B. Liu, Z. D. Hu, Y. Che, "Ultrafast sources: ultrafast lasers produce nanoparticles", Laser Focus World, Vol. 43, 74 (2007) and B. Liu, Z. D. Hu, Y. Che, Y. B. Chen, X. Q. Pan, "Nanoparticle generation in ultrafast pulsed laser ablation of nickel", Applied Physics Letters, Vol. 90, 044103 (2007). In these studies from metal substrates it was found that the ablated material existed predominantly in the form of nanoparticles with a narrow size distribution. A U.S. patent application Ser. No. 11/712,924 filed on Mar. 2, 2007 and published on Jan. 10, 2008 as US publication no. 2008/0006524 also teaches a method of generating nanoparticles from metals and metal oxides in a vacuum and ambient gas and depositing them on a substrate. The inventors have found that a low pulse energy near the ablation threshold is also preferred for formation of organic nanoparticle colloids. It is preferred for the present invention that the pulses have a pulse energy of from 1 nano-Joules to 10 mili-Joules, more preferably from 100 nano-Joules to 10 micro-Joules.

The present inventors have discovered that a high pulse repetition rate is very beneficial for producing nanoparticles according to the present invention from organic source material. A preferred pulse repetition rate is in the range of from 1 Hz to 100 MHz, more preferably 10 kHz to 10 MHz and most preferably 100 kHz to 5 MHz. These high repetition rates are beneficial for at least three reasons. First, these rates produce a multiple pulse effect in high repetition rate pulsed laser ablation. With a repetition rate of 100 kHz or greater, for example, the pulse separation is 10 microseconds or less. This period of time is short enough that the ablated material, before drifting away from the laser focal volume, will receive multiple laser pulses and become highly charged. The inventors discovered stable nanoparticle colloids can be made at such high repetition rates without adding additional stabilizing chemical agents because of this charging. Second, when the ablation process comprises multiple pulses of the ablated material, fragmentation of initially larger particles can occur, resulting in a final size distribution predominated by nanoparticles. Finally, the high repetition rate leads to a high production rate of nanoparticles.

The inventors have also discovered that fast rastering of the laser beam 1 during the ablation process is beneficial in conjunction with the high repetition rate to produce nanoparticles from organic sources. A preferred rastering rate is 0.01 meters per second or greater and more preferred is a rastering rate of 0.1 meters per second or greater. Without such fast rastering of the laser beam 1, the stream of nanoparticles 10 produced by the leading laser pulses will eventually block the subsequent laser pulses by scattering and absorption of the laser beam 1. More importantly, accumulated heating of the liquid 5 due to the high repetition rate can also induce coagulation of the nanoparticles 10.

In addition to the laser parameters described above, the inventors have found that movement of the liquid 5 is also useful in making stable nanoparticle colloids. This is primarily because a dispersed colloidal suspension of nanoparticles 10 in a liquid 5 such as water is essentially in a metastable state, i.e., a kinetically stable state and not a thermodynamically stable state. Flow of the liquid 5 during production helps to reduce a nanoparticle's 10 thermal movement, which may overcome the kinetic barrier to coagulation. Preferably the liquid 5 flow rate is 1 milliliter per second or greater, more preferably 10 milliliter per second or greater. A fast rastering of the laser beam 1 is also beneficial in reducing a nanoparticle's 10 thermal motion.

Figure 2:
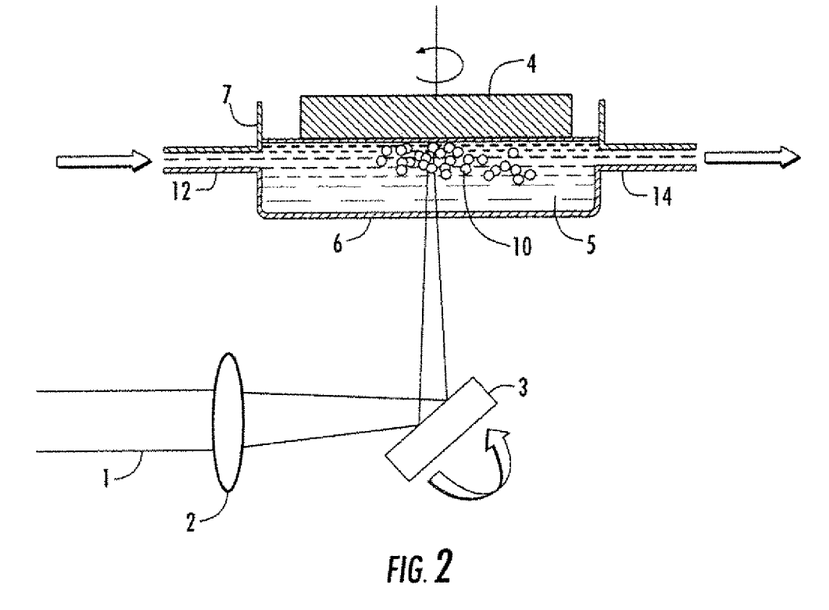
FIG. 2 schematically illustrates an alternative laser-based system for producing organic nanoparticles in a liquid according to the present invention.

FIG. 2 schematically illustrates an alternative laser-based system for producing organic nanoparticles in a liquid in accordance with the present invention. In this embodiment the laser beam 1 is received from a ultrafast pulse source, not shown, and focused by the lens 2. The source of the laser beam 1 can be any suitable pulsed laser source capable of providing a pulse duration, repetition rate and/or power level as discussed above. The focused laser beam 1 then passes from the lens 2 to the guide mechanism 3 for controlling movement of the laser beam 1. The guide mechanism 3 can be any of those known in the art including by way of example piezo-mirrors, acousto-optic deflectors, rotating polygons, vibrating mirror, and prisms. Preferably the guide mechanism 3 is a vibrating minor 3 to enable controlled and rapid movement of the focused laser beam 1. The guide mechanism 3 directs the focused laser beam 1 at the target 4. Preferably the target 4 is a compressed pellet of the organic compound that is being converted into nanoparticles. The compressed pellet can be formed from a variety of powder sources of the organic material. The powdered source material is then compressed into a pellet using a mold and pressure. The bottom of the container 7 serves as glass window 6 to allow the focused laser beam 1 pass through to ablate the organic compound target 4. The target can be submerged into the liquid 5, or the bottom of target 4 can just touch a top surface of the liquid 5. The distance between the bottom of target 4 and glass window 6 can be from several millimeters to preferably less than 1 centimeter. The container 7 includes the inlet 12 and the outlet 14 so the liquid 5 can be passed over the target 4 and so that it can be re-circulated. Flow of the liquid 5 is used to carry generated nanoparticles 10 out of the container 7 to be collected elsewhere. The flow of liquid 5 over the target 4 also cools the laser focal volume. The liquid 5 can be any liquid that is largely transparent to the wavelength of the laser beam 1 and that preferably is a poor solvent for the target material 4. In one embodiment the target 4 can be mounted on a rotating mechanism and spin during the ablation with the spin speed from several revolutions per minute to a several hundred revolutions per minute as shown by the arrow in the figure. As the target 4 rotates, some of the liquid described as the hydrodynamic boundary layer is dragged by the spinning. Liquid flows up, perpendicular to the target 4, from the bottom to replace the boundary layer. The sum results are a laminar flow of liquid 5 towards and across the target 4, and distribution of the generated nanoparticles 10 into liquid 5. This also prevents any gas bubbles generated during the laser ablation from staying on the target 4.

Figure 3:
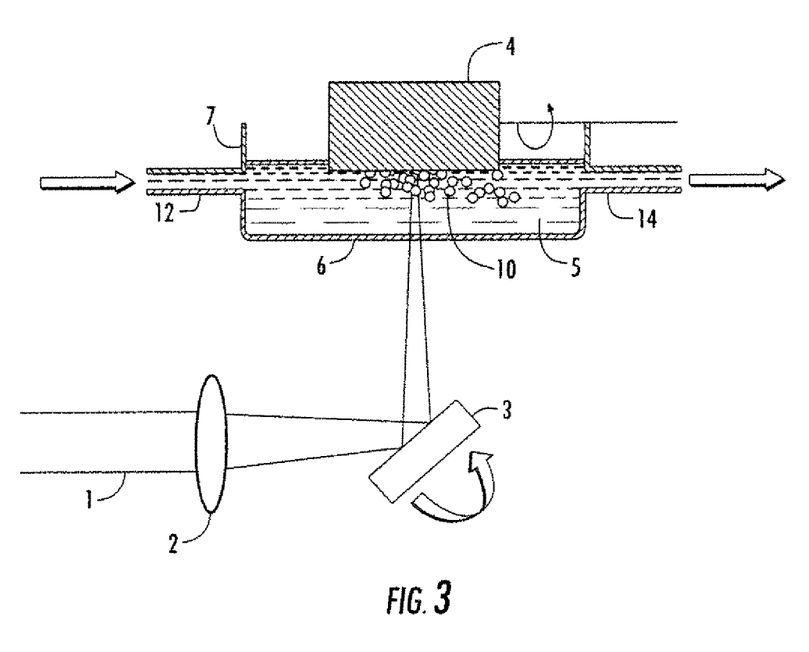
FIG. 3 schematically illustrates a laser-based system for producing organic nanoparticles in a liquid according to the present invention by ablating a side surface of a cylindrical target.

FIG. 3 schematically illustrates another alternative laser-based system for producing organic nanoparticles in a liquid in accordance with the present invention. In this embodiment the laser beam 1 is received from a ultrafast pulse source, not shown, and focused by the lens 2. The source of the laser beam 1 can be any suitable pulsed laser source capable of providing a pulse duration, repetition rate and/or power level as discussed above. The focused laser beam 1 then passes from the lens 2 to the guide mechanism 3 for controlling movement of the laser beam 1. The guide mechanism 3 can be any of those known in the art including by way of example piezo-mirrors, acousto-optic deflectors, rotating polygons, vibrating mirror, and prisms. Preferably the guide mechanism 3 is a vibrating mirror 3 to enable controlled and rapid movement of the focused laser beam 1. The guide mechanism 3 directs the focused laser beam 1 at the target 4. Preferably the target 4 is a compressed cylinder of the organic compound that is being converted into nanoparticles. The compressed cylinder can be formed from a variety of powder sources of the organic material. The powdered source material is then compressed into a cylinder using a mold and pressure. The bottom of the container 7 serves as glass. window 6 to allow the focused laser beam 1 to pass through and to ablate the organic compound target 4. The target 4 can be submerged into liquid 5, or the side surface of target 4 can just touch the top surface of liquid 5. The distance between the side surface of target 4 and glass window 6 can be from several millimeters to preferably less than 1 centimeter. The container 7 includes the inlet 12 and the outlet 14 so the liquid 5 can be passed over the target 4 and so that it can be re-circulated. Flow of the liquid 5 is used to carry generated nanoparticles 10 out of the container 7 to be collected elsewhere. The flow of liquid 5 over the target 4 also cools the laser focal volume. The liquid 5 can be any liquid that is largely transparent to the wavelength of the laser beam 1 and that preferably is a poor solvent for the target material 4. In one embodiment the target 4 is mounted on a rotating mechanism and rotates during the ablation with the rotation speed from several revolutions per minute to a several hundred revolutions per minute as shown by the arrow in the figure. In this layout, the nanoparticles 10 are generated at the side surface of the cylindrical organic compound target 4 instead of at the end surface of the cylindrical target. As the target 4 rotates, it will help to distribute generated nanoparticles 10 into liquid 5, and prevent any gas bubbles generated during the laser ablation from staying on the target 4.

Figure 4:
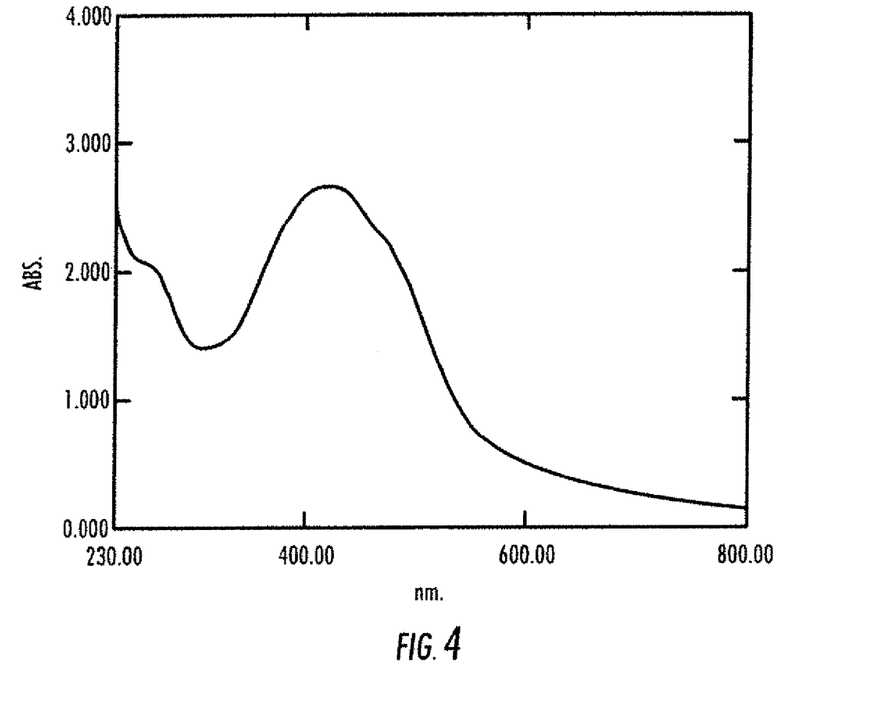
FIG. 4 is a plot of absorption versus wavelength of a curcumin nanoparticle hydrocolloidal dispersion.

In a first experiment curcumin powder, purchased from Sigma Aldrich, was used as the organic source material. The curcumin powder was formed into a pellet of target material by compression in a 0.5 inch in diameter mold using three tons of pressure. The curcumin pellet was then ablated according to the present invention using deionized water as the liquid. The flow rate of the liquid in the container was about 80 milliliters per second. The curcumin pellet was ablated using an ultrafast pulsed laser having a wavelength of 1045 nanometers, using a pulse duration of 500 femtoseconds, a pulse energy of 1 microJoules, a power of 1 W and a pulse repetition rate of 1 MHz. The laser focus spot size was about 30 micrometers in diameter and the fluence is calculated at about 0.14 Joules/cm$^2$. The frequency of the vibrating mirror was 50 Hz with a 4 millimeter trace for 0.4 meters per second. The obtained curcumin nanoparticle hydrocolloidal suspension had a yellow color. FIG. 4 shows an absorption spectrum of the curcumin nanoparticle hydrocolloidal which is represented by an absorption peak centered at about 420 nanometers. The hydrocolloidal contains some large particles as evidenced by the spread of the peak and the background absorbance of the curve. The y-axis is the absorption and the x-axis is the wavelength. Because curcumin does not dissolve in water there is no curcumin in water spectrum that can be used as a reference to compare to the hydrocolloidal curcumin nanoparticles.

Figure 5:
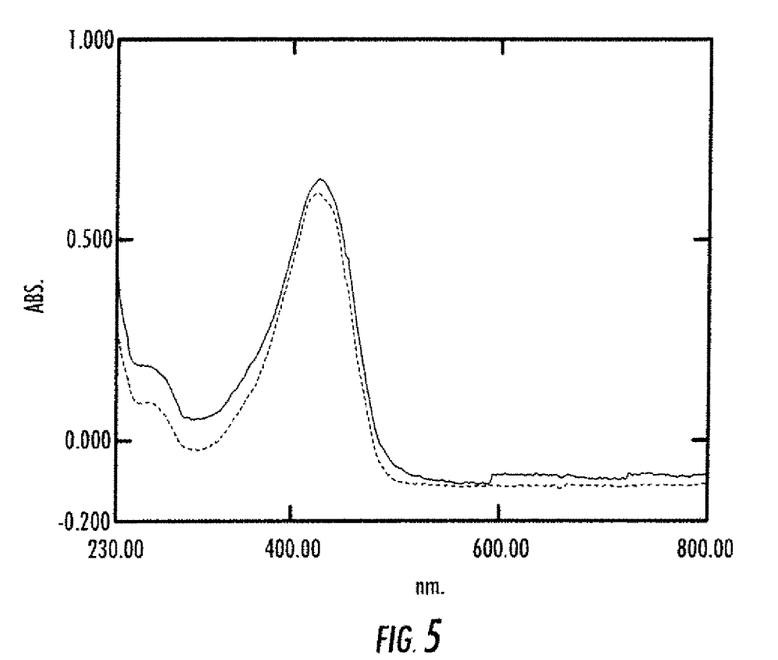
FIG. 5 shows the absorption spectra of a solution of pure curcumin powder dissolved in methanol and the spectra of a curcumin nanoparticle hydrocolloidal prepared according to the present invention mixed with methanol.

Curcumin is dissolvable in methanol, thus the starting curcumin powder was dissolved in methanol at a concentration of $2.5\times10^{-5}$ M to serve as a standard. In addition, 0.1 milliliters of the curcumin nanoparticle hydrocolloidal prepared according to the present invention was mixed with 1.0 milliliters of methanol. The mixture of prepared nanoparticle hydrocolloidal and methanol was a clear yellow colored solution as was the solution of curcumin powder dissolved in methanol. FIG. 5 shows the absorption spectra of each curcumin methanol solution. The solid line trace is the hydrocolloidal sample prepared according to the present invention. The dotted line trace is the curcumin standard. As can be seen the two spectra are virtually identical with a major peak at 420 nanometers indicating the existence of curcumin in the hydrocolloidal sample. The trace with the slightly higher peak at 420 nanometers is from the hydrocolloidal sample prepared according to the present invention. The identical nature of the spectra indicates that ablation of a curcumin pellet in water using a low energy ultrafast pulsed laser according to the present invention does not destroy the curcumin structure, instead curcumin nanoparticles are generated and disperse into water forming a stable curcumin nanoparticle hydrocolloidal suspension.

Figure 8:
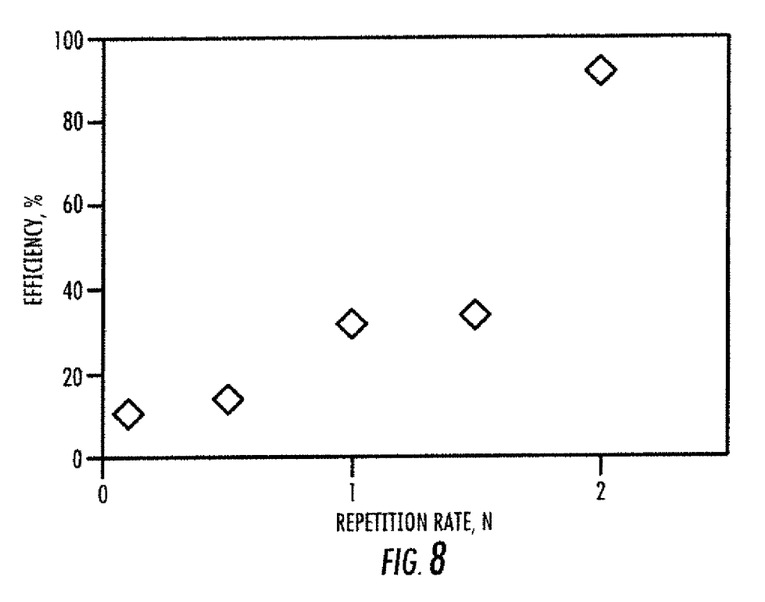
FIG. 8 is a plot of efficiency of nanoparticle production according to the present invention versus laser repetition rate.

It was found that ablation of the curcumin pellet target in water using higher pulse energies generated larger particles and these larger particles tended to precipitate from the hydrocolloidal suspension. Thus, as the pulse energy is increased the number of larger particles increases. These large particles can be easily separated from the hydrocolloidal suspension either by filtration or by centrifugal separation at 2000 rpm for 3 to 5 minutes. Using filter paper to retain the large curcumin aggregates enables them to be separated from the curcumin hydrocolloid. The filter paper is then washed with methanol to dissolve the retained aggregates. For example, Fisher P8 paper with a particle retention size of 25 microns can be used. Using the pure curcumin powder dissolved in methanol an absorbance at 420 nm standard curve can be generated. Then the curcumin level can be determined in both the nanoparticle hydrocolloid and in the filtrate washed off of the filter. Then the efficiency of using laser ablation to generate curcumin nanoparticles can be determined. It was found that the efficiency of production of nanoparticles increased as the laser pulse energy was decreased. FIG. 8 shows the efficiency of producing nanoparticles versus the laser repletion rate. The total power of the laser was fixed at 1 Watt; therefore, an increase of repetition rate represents a decrease of pulse energy. The efficiency was calculated from the amount of nanoparticles in colloidal solution and the amount of particles retained on the filter paper as a percentage of the total. The amounts in each were determined from the absorbance at 420 nanometers of UV-Vis absorption curves for colloid/MeOH and filter paper retained particles dissolved in methanol as described above. If the laser pulse energy is decreased too much, then the production rate is too slow. It is possible to compensate for some of the low production rate at low pulse energies by raising the repetition rate.

Figure 6:
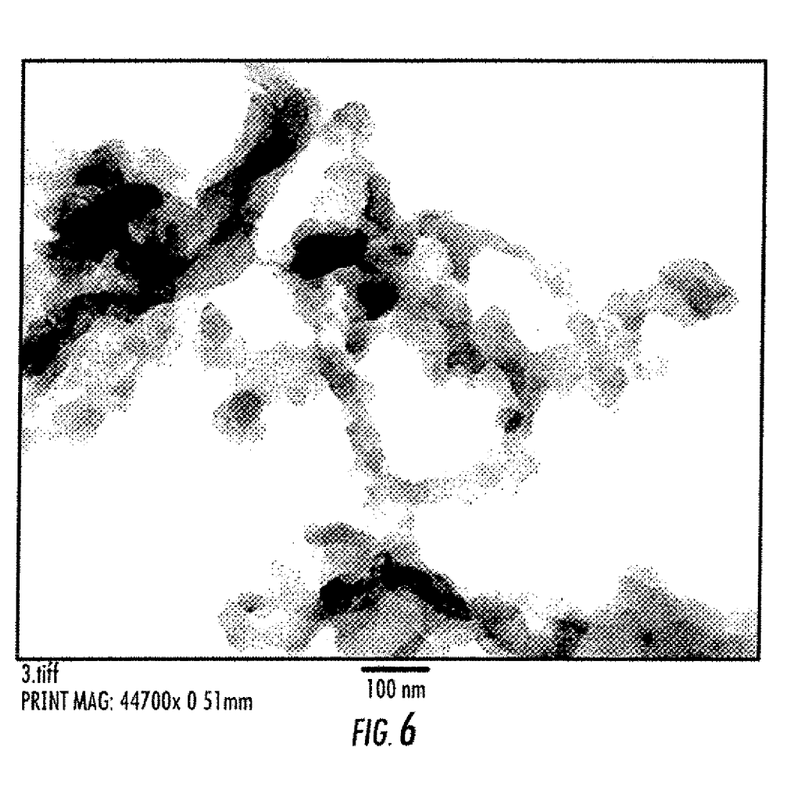
FIG. 6 is a transmission electron microscope (TEM) image of a dried sample of a drop of a curcumin nanoparticle hydrocolloidal prepared according to the present invention on a TEM sampling grid.

FIG. 6 is a transmission electron microscope (TEM) image of curcumin nanoparticles generated from a pellet of curcumin in deionized water according to the present invention. The average power of the laser used was 0.9 W with a repetition rate of 100 kHz, pulse energy of 9 micro-Joules, wavelength of 1045 nanometers, pulse duration of 500 femtoseconds. The laser beam had a focal spot diameter of 50 microns and the raster rate was as described above. The generated nanoparticle hydrocolloidal suspension was filtered through Fisher Scientific's P8 filter paper which has a retention size of 25 microns. A drop of the filtrate was transferred to a TEM sampling grid and dried. Although the curcumin nanoparticles aggregate during the drying process, the original nanoparticles are still recognizable and it can be seen that most have a size of less than 100 nanometers.

Figure 7:
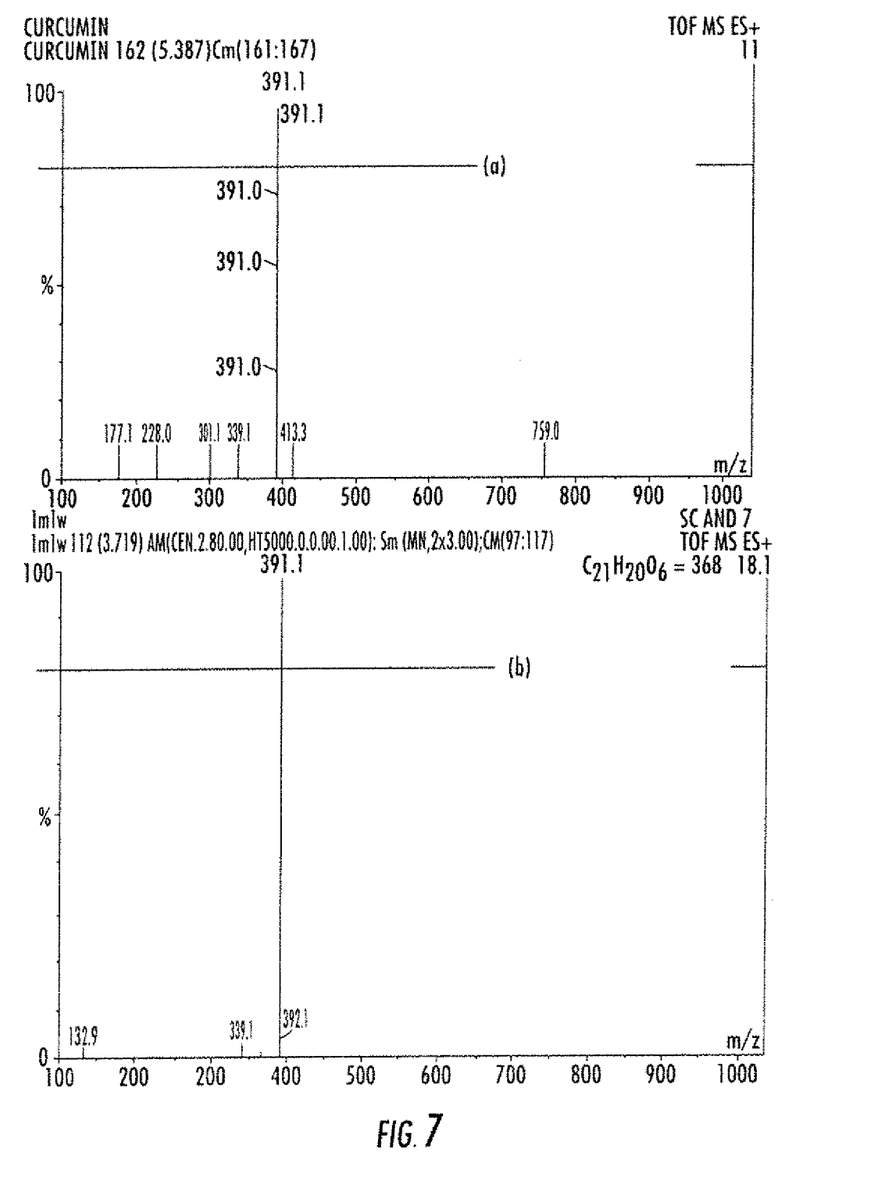
FIG. 7A is a mass spectrum of a pure curcumin powder sample and FIG. 7B is a mass spectrum of a curcumin nanoparticle hydrocolloidal sample prepared according to the present invention.

FIG. 7A is the Mass Spectrum (MS) of pure curcumin starting powder and FIG. 7B is the MS of a curcumin hydrocolloidal sample prepared according to the present invention. The curcumin hydrocolloidal sample was prepared using ultrafast laser ablation according to the present invention in a container with the following laser parameters: 1 Watt of power, repetition rate of 1 MHz, wavelength of 1045 nanometers, 500 femtosecond pulse duration, and the same raster rate as described above. The liquid was deionized water. It is observed that the most intense peaks in both MS tracings are at a mass of 391 for both standard curcumin and the hydrocolloidal sample, which indicates that the curcumin molecules are unchanged during the laser ablation according to the present invention. The major peak at mass 391 can be assigned to the complex of curcumin, mass 368, and sodium, mass 23. The starting curcumin powder was examined using Energy Dispersed Spectroscopy and no existence of sodium in the curcumin powder was found. This indicates that the sodium is introduced into both samples during the MS process. Despite the appearance of sodium on the MS for both standard curcumin and the hydrocolloidal sample, this does not change the fact that laser ablation of the curcumin pellet in water to form the nanoparticle hydrocolloidal did not destroy the molecular structure of the curcumin.

While the present invention has been illustrated using curcumin as the organic target material and deionized water as the liquid it is much more broadly applicable. Any other organic material that can be formed into a target pellet could be used as the target material. Alternatively, as discussed above, the target can be another source of the organic compound material such as: a film of the organic compound that has been deposited onto a substrate; a bulk material of an organic compound with at least one dimension that is larger than 5 mm; a stream of the bulk organic compound which has been ejected from a nozzle into the liquid; or a paste of the bulk organic compound that has been introduced into the liquid. Any of these can serve as the target material in the present invention. In addition, liquids other than deionized water could be used depending on the desired colloidal suspension.

The foregoing invention has been described in accordance with the relevant legal standards, thus the description is exemplary rather than limiting in nature. Variations and modifications to the disclosed embodiment may become apparent to those skilled in the art and do come within the scope of the invention. Accordingly, the scope of legal protection afforded this invention can only be determined by studying the following claims.

We claim:

1. A method for producing a nanoparticle colloidal suspension of organic material dispersed in a poor solvent liquid, the method comprising steps of:
   irradiating a shaped bulk target of an organic compound material with an ultrashort pulsed laser beam having a pulse duration of 500 picoseconds or less and a pulse repetition rate of 10 kHz to 100 MHz, the target mounted during said irradiating over a flow cell holding the liquid so that at least a portion of the target is submerged below the liquid surface, the liquid being substantially transparent at a wavelength of the pulsed laser beam, the irradiation generating a nanoparticle suspension of the organic compound material in the liquid by ablation through the liquid and flow cell, the liquid and nanoparticle suspension being free of stabilizing agents and surface active agents, and the nanoparticle suspension being stable at 25° C. for 7 days; and
   producing a movement of the liquid into and out of the flow cell and across a submerged target surface during said irradiating.

2. The method of claim 1, wherein the pulse duration is from about 10 femtoseconds to 500 picoseconds.

3. The method of claim 1, wherein the pulse duration is from 10 femtoseconds to 200 picoseconds.

4. The method of claim 1, wherein the pulse duration is from 100 femtoseconds to 10 picoseconds.

5. The method of claim 1, wherein the pulse repetition rate is from 10 kHz to 10 MHz.

6. The method of claim 1, wherein the pulse repetition rate is from 100 kHz to 5 MHz.

7. The method of claim 1, wherein the laser beam has a pulse energy ranging from about 1 nano-Joule to 10 milli-Joules.

8. The method of claim 1, wherein the laser beam has a pulse energy ranging from 100 nano-Joules to 10 micro-Joules.

9. The method of claim 1, wherein the laser beam has a laser fluence at a focus spot on the target surface ranging from about 100 micro-Joules/cm$^2$ to 100 Joules/cm$^2$.

10. The method of claim 1, wherein the laser beam has a laser fluence at a focus spot on the target surface ranging from about 10 milli-Joules/cm$^2$ to 5 Joules/cm$^2$.

11. The method of claim 1, wherein the laser beam has a wavelength ranging from about 400 nm to 4000 nm.

12. The method of claim 1, wherein the laser beam has a wavelength of about 1045 nm.

13. The method of claim 1, wherein the nanoparticles have an average diameter of 100 nm or less.

14. The method of claim 1, further comprising forming the bulk target to have a cylinder shape by compressing a powder of the organic compound material.

15. The method of claim 1, wherein the target has a size of at least 1 mm in at least one dimension.

16. The method of claim 1, wherein the target has a size of at least 5 mm in at least one dimension.

17. The method of claim 1, wherein the liquid is deionized water.

18. The method of claim 17, wherein the deionized water has a resistivity greater than 0.05 MOhm.cm.

19. The method of claim 1, wherein the relative movement is provided at a rate equal to or greater than 1 mL/s.

20. The method of claim 1, wherein the liquid movement is produced by a liquid pump.

21. The method of claim 1, wherein the moving liquid cools a region around the bulk target and transports the nanoparticles away from the region and toward a collection location.

22. The method of claim 1, wherein the flow cell has an optical window transparent to the laser beam.

23. The method of claim 1, further comprising moving the laser beam relative to the target by at least one optical component during said irradiating.

24. The method of claim 23, wherein the optical component is a vibrating mirror.

25. The method of claim 24, wherein the vibrating mirror has a vibrating frequency of 10 Hz or greater and an angular amplitude of 0.1 mrad or greater so as to provide a movement speed of the beam on the target surface of 0.01 m/s or greater.

26. The method of claim 1, wherein said mounting is on a rotating mechanism spinning the target during said irradiating.

* * * * *